US00PP12956P2

(12) United States Plant Patent
Acosta

(10) Patent No.: US PP12,956 P2
(45) Date of Patent: Sep. 17, 2002

(54) PHILODENDRON PLANT NAMED 'BRASIL'

(75) Inventor: Ruben Ernesto Acosta, Holambra (BR)

(73) Assignee: Twyford International, Santa Paula, CA (US)

( * ) Notice: Subject to any disclaimer, the term of this patent is extended or adjusted under 35 U.S.C. 154(b) by 0 days.

(21) Appl. No.: 09/484,662

(22) Filed: Jan. 18, 2000

(51) Int. Cl.[7] ..... A01H 5/00
(52) U.S. Cl. ..... Plt./381

(58) Field of Search ..... Plt./381

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Philodendron plant named 'Brasil', characterized by its unique dark green and yellow green variegated leaves; elongated leaf apices; and young stems and leaf petioles that are initially reddish pink becoming reddish orange and eventually light green with subsequent development.

1 Drawing Sheet

BACKGROUND OF THE INVENTION

The present Invention relates to a new and distinct cultivar of Philodendron plant, botanically known as *Philodendron scandens oxycardium* and referred to by the cultivar name Brasil.

The new Philodendron is a naturally-occurring whole plant mutation of an unnamed selection of *Philodendron scandens oxycardium*. The new Philodendron was discovered by the Inventor in a controlled environment in Holambra, Brazil, as a single plant within a planting of the unnamed selection in 1991. The selection of this plant was based on its unique green and yellow green variegated foliage.

Asexual propagation of the new cultivar by cuttings at Holambra, Brasil, and Sebring, Fla., has shown that the unique features of this new Philodendron are stable and reproduced true to type in successive generations.

SUMMARY OF THE INVENTION

The following traits have been repeatedly observed and are determined to be the unique characteristics of 'Brasil'. These characteristics in combination distinguish 'Brasil' as a new and distinct cultivar and distinguish it from the parent selection:

1. Plants of the new Philodendron have unique dark green and yellow green variegated leaves.

2. Plants of the new Philodendron have elongated leaf apices.

3. Young stems and leaf petioles of plants of the new Philodendron are initially reddish pink becoming reddish orange and eventually light green with subsequent development.

The cultivar Brasil has not been observed under all possible environmental conditions. The phenotype may vary somewhat with variations in environment such as temperature, light intensity and/or fertilizer rate, without, however, any variance in genotype.

BRIEF DESCRIPTION OF THE PHOTOGRAPH

The accompanying colored photograph illustrates the overall appearance of the new Philodendron, showing the colors as true as it is reasonably possible to obtain in colored reproductions of this type. Colors in the photograph may differ slightly from the color values cited in the detailed botanical description which more accurately describe the actual colors of the new Philodendron. The photograph comprises a side perspective view of typical 16 to 18-week old plants of 'Brasil' grown in a 20-cm hanging basket container.

DETAILED BOTANICAL DESCRIPTION

The following observations, measurements and values describe plants of the new Philodendron grown in 20-cm hanging basket containers, with about eight rooted cuttings per basket, in Sebring, Fla., with day temperatures averaging 27° C., night temperatures averaging 13° C., and light levels about 1,500 to 2,000 foot candles..

Color references are made to The Royal Horticultural Society Colour Chart except where general terms of ordinary dictionary significance are used.

Botanical classification: *Philodendron scandens oxycardium* cultivar Brasil.

Parent: Naturally-occurring whole plant mutation of an unnamed selection of *Philodendron scandens oxycardium*, not patented.

Propagation:

*Type*.—By cuttings.

*Time to initiate roots*.—Summer: About 10 days at 25 to 35° C. Winter: About 14 days at 15 to 30° C.

*Time to produce a rooted liner*.—Summer: About 45 days at 25 to 35° C. Winter: About 60 days at 15 to 30° C.

*Root description*.—Thick, fleshy; typical of species.

Plant description:

*Appearance*.—Low-growing; cascading, trailing, decumbent. Full plants with dense foliage.

*Crop time*.—From planting rooted cuttings, about 16 to 18 weeks are required to produce finished plants in 20-cm hanging basket containers.

*Plant height*.—About 14 cm.

*Plant spread*.—About 55 cm.

*Stems*.—Length: About 52 cm. Diameter: About 5.5 mm. Internode length: About 7.7 cm. Texture:

Smooth. Branching: Branching enhanced by pinching; potentially branching at every node. Color: Young stems: Reddish pink, close to 182B to 182C, to reddish orange, close to 171A. Older stems: Green, 144A to 146A.

*Foliage description.*—Arrangement: Alternate. Length: About 11.3 cm. Width: About 8.5 cm. Shape: Cordate. Apex: Acuminate, elongated. Base: Cordate. Aspect: Mostly flat to undulate; mostly horizontal. Texture: Smooth, waxy; somewhat glossy. Color: Dark green ground color with yellow green to light green central variegation pattern. Variegation pattern longitudinal to the leaf axis and irregular. Low light conditions enhance variegation development.

Young and fully expanded foliage, upper surface: Dark green, 147A; central longitudinal stripe, yellow green, close to 145A, to lighter green, 146A to 146B to 146C to 147B. Occasionally, some areas close to 153A in color. Young and fully expanded foliage, lower surface: Dark green, 147A to 147B; central stripe, close to 145A to 146D. Petiole: Length: About 7.3 cm. Diameter, at base: About 4 mm. Shape: Channeled. Aspect: Mostly upright. Strength: Strong, but flexible. Color: Young foliage: 182A to 182B. Fully expanded foliage: Mostly green, 144A; channel, 146A.

Inflorescence description: Inflorescence development has not been observed on plants of the new Philodendron.

Disease resistance: Resistance to pathogens common to Philodendron has not been observed on plants of the new Philodendron.

It is claimed:

1. A new and distinct cultivar of Philodendron plant named 'Brasil', as illustrated and described.

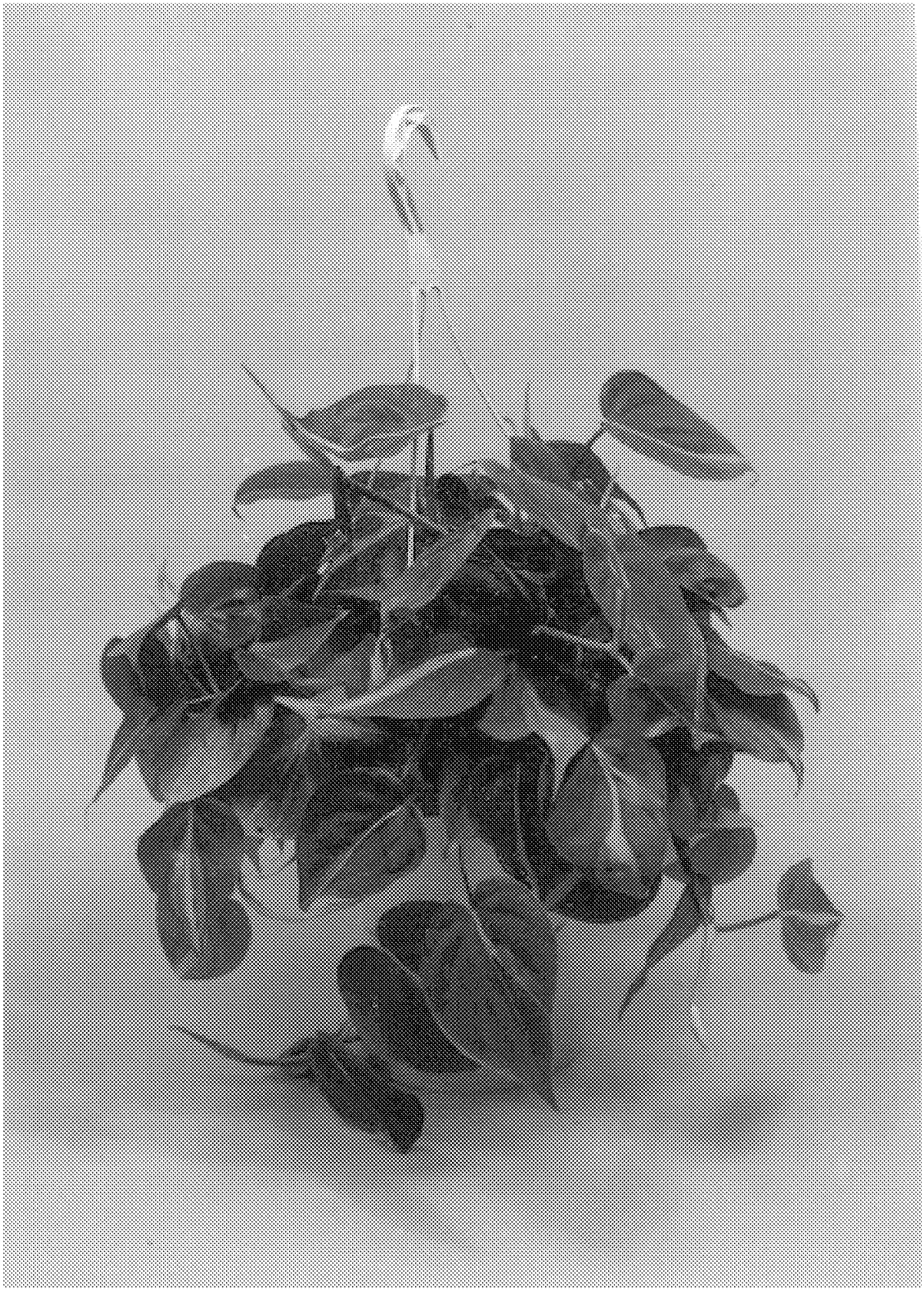

* * * * *